United States Patent [19]

Stroterhoff

[11] 3,966,412

[45] June 29, 1976

[54] LEWISITE DETECTION SAMPLER AND METHOD

[75] Inventor: Howard L. Stroterhoff, Towson, Md.

[73] Assignee: The United States of America as represented by the Secretary of the Army, Washington, D.C.

[22] Filed: Mar. 25, 1975

[21] Appl. No.: 561,723

[52] U.S. Cl. .......................... 23/232 R; 23/253 TP; 23/254 R; 252/408; 73/421.5 R
[51] Int. Cl.² ................. G01N 21/06; G01N 21/12
[58] Field of Search ............ 23/253 TP, 259, 254 R, 23/232 R; 252/408; 73/421.5 R

[56] References Cited
UNITED STATES PATENTS

| 3,689,224 | 9/1972 | Agnew et al. .................... 23/253 TP |
| 3,697,227 | 10/1972 | Goldstein et al. ................ 23/253 TP |
| 3,726,645 | 4/1973 | Kaczmarek ..................... 23/253 TP |
| 3,740,196 | 6/1973 | Stroterhoff ..................... 23/253 TP |

Primary Examiner—R.E. Serwin
Attorney, Agent, or Firm—Nathan Edelberg; Robert P. Gibson; Robert W. Church

[57] ABSTRACT

A self-contained sampler for use in the detection of low concentrations of lewisite; i.e., chlorovinyldichlorarsine in air through use of a sensitive colorimetric method.

2 Claims, 3 Drawing Figures

LEWISITE DETECTION SAMPLER AND METHOD

DEDICATORY CLAUSE

The invention described herein may be manufactured, used and licensed by or for the Government for Governmental purposes without the payment to me of any royalty thereon.

SUMMARY OF THE INVENTION

My invention relates to a self-contained sampler for detecting low concentrations of lewisite in air by means of a sensitive colorimetric method. The sampler of the instant invention provides a simple, specific and reliable chemical spot test for lewisite; i.e., chlorovinyldichlorarsine in air which can be operated by unskilled personnel in the field and is compact enough to be carried in one's pocket. The sampler may be used either independently or in conjunction with a multipurpose chemical spot test system similar to that disclosed in the U.S. Pat. No. 3,726,645.

The sampler colorimetric detector of this invention is a marked improvement over prior art contaminant detectors, such as the L crayon detectors similar to those disclosed in U.S. Pat. Nos. 2,926,072 and 2,929,791 in its ease and economy of fabrication from inexpensive, readily available materials and in its simplicity of reaction.

The primary object of this invention is to provide a simple, effective and reliable self-contained sampler detection for use in a method of qualitatively detecting low concentrations of lewisite vapors in air.

A further object of this invention is to provide a one step reaction wherein lewisite vapors are contacted with a strong alkali to generate acetylene and in turn react the acetylene with a cuprous salt to form brownish-red cuprous acetylide.

A still further object of this invention is to provide a portable detector for use in process plants, laboratory and in the field by unskilled persons.

A further object of this invention is to provide a disposable sampler detector which is inexpensive and readily fabricated from available materials.

A still further object of this invention is to provide a portable detector for use in process plants, laboratory and in the field by unskilled persons.

These and other objects and advantages will become apparent from the following detailed description of the invention.

Figure 1:
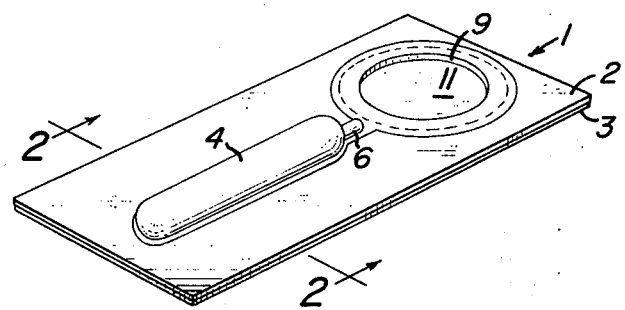
FIG. 1 is a view showing the entire sampler detector assembly of this invention.
Figure 2:
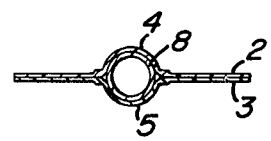
FIG. 2 is a cross-sectional view of the assembly of FIG. 1 taken along line 2—2.
Figure 3:
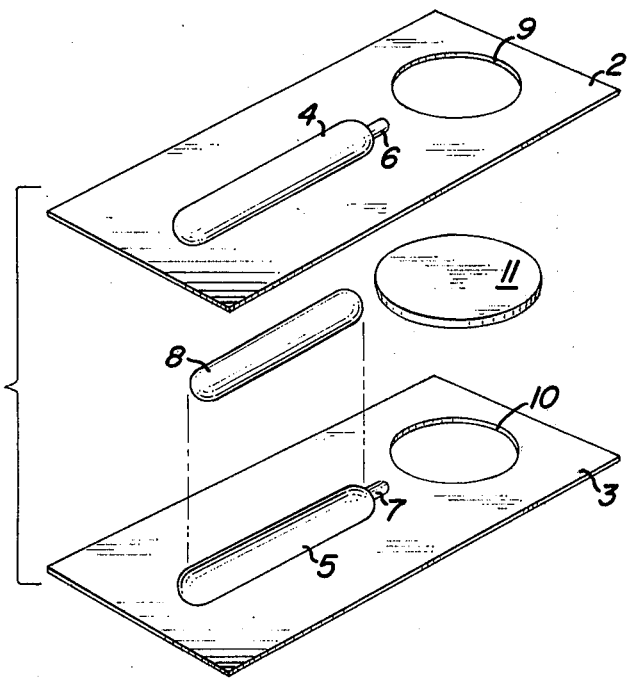
FIG. 3 is an exploded view of the sampler assembly shown in FIG. 1.

My invention, as shown in FIGS. 1 to 3, will now be described in more detail as follows:

The sampler detector at 1 of FIG. 1 comprises upper and lower pre-formed; e.g., vacuum formed, plastic bodies 2 and 3, respectively, which are preferrably identical, are fitted in a matched relationship. The plastic; e.g., polyethylene bodies 2 and 3, shown in FIG. 3, have molded or stamped recesses 4 and 5, respectively, which when matchingly fitted will form the seated inclosure for the frangible thin walled glass reactant ampule 8 as seen in FIG. 2. The recesses 4 and 5 are tapered at one end to form channel recesses 6 and 7 which are orientated towards silica gel paper spot 11 which is disposed between apertures 9 and 10 in the formed plastic bodies 2 and 3, respectively. The frangible reactant ampule 8 contains a 0.3 ml reagent solution consisting essentially of cupric carbonate, arsenious oxide, sodium hydroxide and piperidine in distilled water. The preferred reagent solution consists of 0.2g cupric carbonate, 6.0g arsenious oxide, 12.0 g sodium hydroxide, 1.0 ml piperidine and 100.0 ml distilled water. The paper spot 11 is a ¾ in. silica gel paper spot.

In operation, frangible ampule 8 constructed, for example, from thin walled glass is crushed by applying direct pressure to the ampule seated enclosure defined by matchingly fitted recesses 4 and 5. Upon rupture of the ampule, the 0.3ml reactant solution of cupric chloride, arsenious oxide, sodium hydroxide and piperidine in distilled water is forceably squeezed through the channel defined by matchingly fitted tapered recesses 6 and 7 to throughly wet the detector silica gel paper spot 11. The wetted detector paper spot 11 is exposed to the environment to be tested for lewisite vapors through aperatures 9 and 10 in the plastic bodies 2 and 3. If lewisite vapors are present they are absorbed on the silica gel paper spot 11, resulting in a color change in the paper spot from white to brownish-red. The color change itself is based upon the reaction of lewisite vapors in contact with strong alkali to generate acetylene, which in turn reacts with cuprous salt to form cuprous acetylide, which is brownish-red in color. Applicant, through his invention, has thus achieved the hitherto unobtainable reaction of lewisite with a strong alkaline solution containing cuprous ions in a one step process.

The particular details of the method of construction of the sampler unit, size and shape of the sampler, do not form a critical part of this invention and can be varied within the scope of the invention. Similarly, the sampler may be formed from two plastic bodies, only one of which contains recesses, all in one plane, with the other body forming a flat surface therewith, so as to form a seated enclosure through which pressure can be applied to rupture the ampule. The orientation and length of the channel recess can also be varied so long as it provides a means for flowing the reactant solution to throughly wet the silica gel paper spot.

It is obvious that other modifications can be made of my invention, such as for example, use of the invention as an acetylene detector, and I desire to be limited only by the scope of the appended claims.

I claim:

1. A method of detecting chlorovinyldichlorarsine vapors in the surrounding atmosphere comprising the steps of placing a white silica gel paper spot and a frangible thin walled ampule containing a reactant solution consisting essentially of cupric carbonate, arsenious oxide, sodium hydroxide, piperidine in an aqueous solution of distilled water, in a recessed plastic film container means having an aperature means in both the upper and lower surfaces for exposing said silica gel paper spot to the atmosphere to be tested, exposing said silica gel paper spot to the atmosphere suspected to contain chlorovinyldichlorarsine, simultaneously crushing the reactant containing ampule to flow the reactant therein to the silica gel paper spot; reacting the reactant solution and any chlorovinyldichlorarsine absorbed in the silica gel paper spot to produce a color change in the white silica gel paper to a color spectrum of brownish-red to indicate the presence of chlorovinyldichlorarsine vapors in the tested atmosphere.

2. The method of claim 1 wherein the reactant ampule contains 0.3ml of a reagents solution of 0.2g cupric carbonate, 6.0g arsenious oxide, 12.0g sodium hydroxide and 1.0ml piperidine dissolved in 100.0 ml distilled water.

* * * * *